US006720469B1

United States Patent
Curtis et al.

(10) Patent No.: US 6,720,469 B1
(45) Date of Patent: Apr. 13, 2004

(54) CELL ADHESION

(75) Inventors: Adam Sebastian Genevieve Curtis, Glasgow (GB); Christopher David Wicks Wilkinson, Glasgow (GB)

(73) Assignee: The University Court of the University of Glasgow (GB)

( * ) Notice: Subject to any disclaimer, the term of this patent is extended or adjusted under 35 U.S.C. 154(b) by 0 days.

(21) Appl. No.: 09/623,751

(22) PCT Filed: Mar. 10, 1999

(86) PCT No.: PCT/GB99/00721

§ 371 (c)(1), (2), (4) Date: Jan. 23, 2001

(87) PCT Pub. No.: WO99/45860

PCT Pub. Date: Sep. 16, 1999

(30) Foreign Application Priority Data

Mar. 11, 1998 (GB) .............................................. 9805214

(51) Int. Cl.[7] .................................................. A61F 13/00
(52) U.S. Cl. .............................. 602/41; 602/42; 602/47
(58) Field of Search .............................. 435/289.1, 366; 604/304–308; 602/41–59; 623/1, 2, 11, 12, 16, 22, 8, 17

(56) References Cited

U.S. PATENT DOCUMENTS 5,011,494 A * 4/1991 von Recum et al. .......... 623/11
5,061,281 A * 10/1991 Mares et al. ................... 623/11
5,213,742 A 5/1993 Conston et al.

FOREIGN PATENT DOCUMENTS

| DE | 31 16040 A 1 | 11/1982 |
| EP | 0 359 575 A2 | 3/1990 |
| EP | 0 790 042 A2 | 8/1997 |
| WO | WO 92/10218 | 6/1992 |
| WO | WO 95/12369 | 5/1995 |

OTHER PUBLICATIONS

Wojciak–Stothard, Beata, et al., *Guidance and Activation of Murine Macrophages by Nanometric Scale Topography*, Experimental Cell Research, vol. 223, pp. 426–435 (1996).

International Search Report, International Application No. PCT/GB99/00721.

* cited by examiner

Primary Examiner—Kim M. Lewis
(74) Attorney, Agent, or Firm—Myers Bigel Sibley & Sajovec

(57) ABSTRACT

A biocompatible substrate for use as a resorbable or non-resorbable implant, graft, prosthesis, etc., has an array of projections or pits of nanometer dimensions on a surface thereof, which resist attachment of cells. Typically the projections or pits are 10–250 nm in size and at spacings of 20–500 nm. The substrate may additionally have areas where cell adhesion is promoted.

14 Claims, 2 Drawing Sheets

Embossing Process

E - beam written sample

Resist
Silicon Substrate

Die or Master

Evaporated metal pillars

Embossing Stack

Apply pressure and heat to GTI
Plastic heated to approximately its Glass Trans. Temperature Embossed Plastic Sample Holes embossed into plastic

CELL ADHESION

TECHNICAL FIELD

The invention relates to biocompatible substrates having a surface topography which has a low tendency for cells to adhere thereto. This has particular application for the production or prostheses or implants requiring low adhesion of cells.

BACKGROUND OF THE INVENTION

Many cell types have been shown to respond by shape change, and orientation to shapes such as fibres, grooves, pits and ridges; and by accelerated movement.

However, little is known about the underlying mechanisms behind this widespread reaction of cells. Explanations of contact guidance have tended to proceed along a coherent line of thought, advancing through three successive stages. First, recognising that cells will not bend or extend their microfilaments across topography that offers the cells relatively sharp angles (greater than about 10°). Secondly, through the realisation that this is a probabilistic phenomenon to the appreciation that cells develop cytoskeletal polymerisation where cells contact discontinuities in the substratum. These ideas suggest that alignment of cells is a reaction of cytoskeleton to topography. An alternative idea is that the adhesion points of the cell, the focal contacts, are prepositioned. None of these ideas explain the nature of the interaction, presumably a signalling event, between substratum and focal contact and/or cytoskeleton.

Since the reactivity of cells to topographic stimuli changes subtly with the exact dimensions of the substrate it was of interest to discover how small a feature would lead to reactions in cells. It has been shown that cells react to linear features with widths as narrow as 130 nm but clearly it is of interest whether smaller scale topography can be sensed by cells.

Grooves 5 microns wide but only 3 nm high caused a marked reaction in macrophage cells. A preliminary report was published by Wojciak-Stothard e a., Experimental Cell Research 223, 426–435 (1996).

SUMMARY OF THE INVENTION

Generally speaking, the present invention is based on the surprising observation that surfaces having a pattern of tiny projections, usually of nanometer dimensions, inhibit the adhesion of cells thereto. This has application in the preparation of surfaces which resist the adhesion of cells.

A particular aspect of the present invention provides a biocompatible substrate having a surface comprising an array of projections or pits, said projections being of a size and spacing such that cells have a low tendency to attach to the surface.

It is envisaged that the substrate will be introduced into a living or other biologically sensitive environment and is therefore to be formed of a biocompatible material. Biocompatible materials (including but not restricted to biodegradable and bioabsorbable materials) are well known in the art and will be chosen having regard to the particular biological environment into which they are to be introduced.

It is known that certain surface features promote cell adhesion thereto and can preferentially orient cell growth, particularly along the directions of grooves and ridges of micrometer dimensions. On the other hand, the present invention allows surfaces to be provided which have a reduced tendency of cell adhesion thereto. In this way, the tendency of cells to adhere or not to a particular surface can be controlled. The process can also be used to build complex tissue structures with seeding of one cell type into gaps in another cell type. For example, where the substrate includes areas of projections/pits and planar areas, cells can be preferentially adhered to the planar areas. An adhesive material (e.g. laminin) may then be coated thereon, and further cells of a different type applied thereto. The further cells adhere preferentially to the laminin-coated areas having projections/pits and avoid adhering to the pre-existing monolayers of cells (over the planar areas). Generally, the low adhesion tendency is less than 50%, particularly less than 30% of that of a corresponding planar surface. Biocompatible substrate on which it may be desirable to inhibit cell adhesion include implants, grafts and prostheses introduced into the vascular system, gastrointestinal tract, lung alveolae, synovia, connective tissue and in the eye or gum and in any part of the body which should normally have void spaces filled with liquid or gas but does not—as a consequence of injury or disease. A particular application is to prevent adhesion of undesired cells to ligaments under repair. For example, a biocompatible substrate for ligament repair may be patterned on an inner surface intended to be wrapped around the ligament with a surface topography intended to promote repair of the damaged ligament (see our patent application PCT/GB95/00350); and may be patterned with a surface topography on the outer side intended to prevent undesired adhesion of other types of cells to the outside of the ligament which would reduce its mobility. In other applications, a sheet-like substrate may be patterned on both sides with adhesion-reducing projections or pits, which may be used as a separation layer to prevent two adjacent structures adhering to each other.

According to the present invention, it has surprisingly been found that projections or pits of nanometer dimensions can inhibit cell adhesion. Generally, the cross sectional dimension and height of each projection is in the range 10–250 nm, particularly in the range 20–100 nm and especially 25–75 nm. Corresponding dimensions apply to pits. A projection is characterised by having an area of reduced height all around it. A pit has an area of increased height all around it. The projection or pit may be of any cross-section, including circular, oval, square, rectangular, polygonal etc.

The projections or pits will be present in an array, which may be in any chosen pattern, such as a square pattern, a rectangular pattern, a circular pattern, a rosette pattern, a random pattern etc. As will be demonstrated hereafter, the center-to-center spacing of the projections or pits can be a determinative factor in controlling the degree of resistance to cell adhesion, with wider spacings favouring reduced cell adhesion. The spacing is generally in the region 20–500 nm, particularly 40–300 nm, especially 75–200 nm.

The projections or pits will be present in an array, which may be in any chosen pattern, such as a square pattern, a rectangular pattern, a circular pattern, a rosette pattern, a random pattern etc. As will be demonstrated hereafter, the centre-to-centre spacing of the projections or pits can be a determinative factor in controlling the degree of resistance to cell adhesion, with wider spacings favouring reduced cell adhesion. The spacing is generally in the region 20–500 nm, particularly 40–300 nm, especially 75–200 nm.

The biocompatible substrate may, if desired, be formed of a resorbable material which becomes resorbed into the living tissue within a chosen period of time, usually a number of days, Following implantation. For example, a substrate intended to prevent adhesion of tissue structures during a healing process could become resorbed after fulfilling its function. Often the need to prevent such undesired cell adhesion only occurs for a limited time after injury or surgical intervention, so in many cases a short-lived form of treatment is appropriate. Bioresorbable materials are well known in the art and include compounds such as glycolide-co-lactide polymers.

The nano-substrate can be formed by techniques well known in the manufacture of structures of nanometer dimensions, such as those used in fabrication of semi conductor microcircuits and/or in the production of compact discs. Typically, the process employs lithography followed by etching to produce the nanometric topography, either directly into the material or so as to form a master for patterning softer materials by embossing, casting or moulding. Such techniques are described in more detail hereafter. Materials suitable for direct patterning include hard materials such as silicon, silica and perspex. Generally, materials to be produced by mechanical transfer (e.g. embossing, casting or moulding) are polymeric materials, which may be optionally heated.

The invention also relates to a master for mechanical transfer of projections or pits onto a substrate.

DETAILED DESCRIPTION OF THE INVENTION

Figure 1:
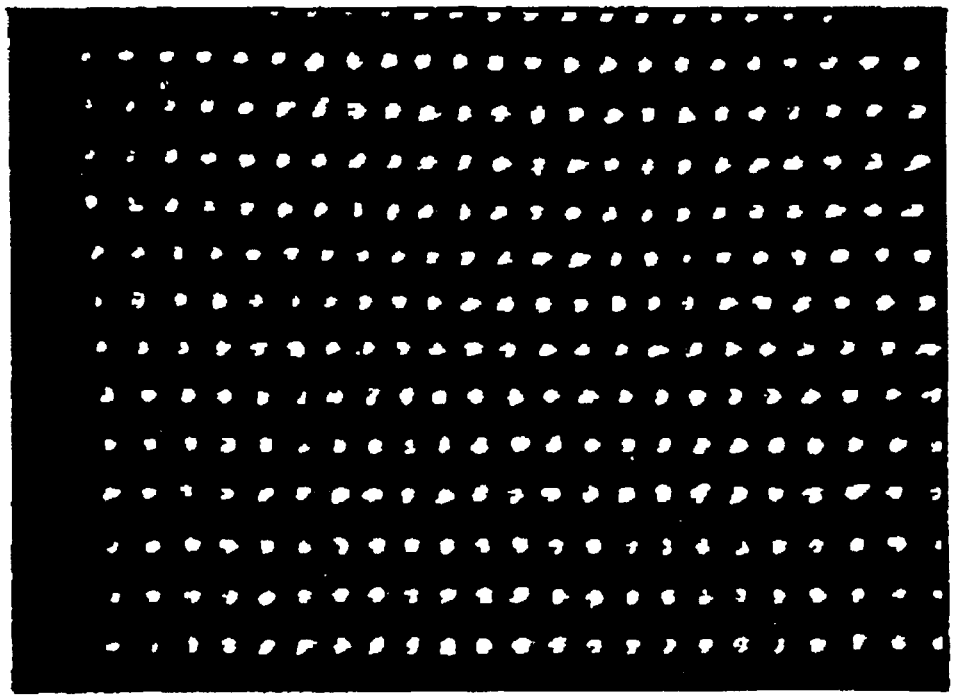
FIG. 1 presents a scanning electron microscopy (SEM) of pillar topography according to the present invention.

Embodiments of the present invention will now be described by way of example only.

GENERAL PRODUCTION METHODS

There are two routes to the formation of such surfaces:
1. For Hard Materials Such as Metal, Ceramics and Glasses The basic technique is to use lithography to define the pattern and etching transfer the pattern into the underlying substrate. The lithography used has to have the desired resolution required to make the pattern for the pillars that are between 10 and 250 nm in diameter. Electron beam and ion beam direct write lithography and electron ion projection and X-ray printing are all suitable.

The lithographic process defines a pattern in a suitable radiation-sensitive resist. This resist may be used directly as a mask for the subsequent etching process, or it may be used as an intermediate mask to transfer the pattern into any intermediate layer, which acts as the mask for the etching process, or it may be used as a stencil which after the deposition of an intermediate layer. The resulting etch resistant mask is then used to allow transfer of the pattern into the hard material. This transfer is done by etching that may be done using chemicals in liquid form or by using ions that form a volatile product with the material.

As an example, the formation of pillars in fused silica proceeds as follows:
  (a) The fused silica is coated with 50 nm of titanium by thermal evaporation in vacuum. The pattern consisting of 50 nm diameter circles on 100 nm center-to-center spacing repeated over an area of 10 by 10 mm is written using an electron beam lithographic machine (leica Beamwriter HR-5) onto an electron sensitive resist, PM114. The is a negative resist, so after exposure and development, circles of resist are left on the titanium.
  (b) The titanium is etched in an electron cyclotron resonance/reactive ion etching machine using the negative resist as a mask. Silicon tetrachloride at a flow rate of 15 sscm gives a pressure of 4 mTorr. The microwave power is 150W, the rf power 24W and the dc bias observed −88V 0.4 minutes is required to etch the 50 nm of titanium.
  (c) The titanium is then used as an ion-resistant mask in reactive ion etching of the silica. In a Oxford Plasmatech RIE 80 etching machine, typical etching conditions are: High purity $CH_3$ gas at pressure point of 15 mTorr, flow rate of 20 sccm, 150 W rf at 13.6 MHz, 420 V. bias.
  (d) The titanium is removed in HF leaving pillars of silica.
2. For Polymeric Materials by Mechanical Transfer While the process above can be adapted for some polymeric materials, it is often preferable to use mechanical transfer by embossing, casting or moulding (including injection moulding) with a die of the correct shape. The die itself can be made by method 1 (suitable for hard materials). Embossing involves heating the plastic to less than its melting temperature and pressing the die into the plastic. In casting, the plastic is dissolved in a suitable solvent, poured over the mould and after evaporation of the solvent, peeled off the die. In moulding, plastic is melted over the die with some pressure applied in the case of injection moulding.

It is possible to make the die in alternative ways: electron beam irradiation of perspex can itself produce raised regions.

As an example, the formation of pits in cellulose acetate is as follows:
  (a) A die of 50 nm pillars 100 nm high is formed in fused silica as described above.
  (b) The 10 by 10 mm die is placed below a sheet of 1 mm thick cellulose acetate with a plain fused silica microscope slide above.
  (c) The sandwich is clamped with a simple toolmaker's clamp and heated to 100° C.
  (d) The sandwich is removed from the oven, the clamp pressure re-adjusted to a given setting using a torque wrench, and the whole allowed to cool.
  (e) The clamp is released leaving an embossed polymeric sheet, ready for sterilisation and use with cells.

The procedure is described for cellulose acetate. It works well with a variety of thermo-setting polymers, including biodegradable (i.e. resorbable) polymers. A suitable temperature has to be found for each material—30 degrees less the glass transition is found to be good starting point for experimentation.

The process can be adapted to produce either pillars or pits.

Effect of Surface on Cell Adhesion

When cells from a fibroblast cell line, are allowed to settle onto a surface patterned inzo 50 nm pillars as described above and on a planar substrate, the adhesion of the cells is markedly lower on the patterned surface.

DETAILED PRODUCTION METHODS
1) Cells

The macrophage line P388D1 was grown in RPMI 1640 medium. Epitena (Wojciak-Stothard ea. J. Materials Science, 6, 266–271 (1995) were grown from cultures isolated from rat flexor tendon in the same medium grown for 20–30 passages. B10.D2.PCE endothelia were obtained from laboratory stocks and grown in Hams F10 medium with 3% fetal calf serum and insulin-transferrin-selenite supplement.

The fibroblast line BHK 21 C13 and a human skin fibroblast line, recently derived in this laboratory, were grown from laboratory stocks in Minimal Essential Medium (MEM) plus 10% fetal calf serum and trypotosephosphate broth. Suspensions of these cells were prepared by typsinisation in 200 BAEE unit trypsin in calcium and magnesium ion-free Hanks medium following washing of the cells with 0.001M EDTA in calcium and magnesium ion-free Hanks. The suspensions were plated out at low population density in serum-containing medium.

2) Microscopy

The cells were observed by optical phase contrast microscopy and the structures by scanning electron microscopy (SEM) and by atomic force microscopy (AFM) Images of pillar topography taken on an SEM are shown in FIG. 1.

3) Measurement of Adhesion

Cell suspensions of the P388D1 cells were prepared by shaking the cultures vigorously followed by centrifugation to remove the old medium and resuspension in RPMI medium. Epitenon and endothelial cells were trypsinised as described above.

Adhesion measurements on nanopillars were done with 1 hour exposure of the cells to the substratum at 37C after trypsinisation of the epitenon cells. Unattached cells were then removed by gentle shaking and pouring off the medium. The attached cells were counted and adhesion is expressed as a percentage of the maximal possible attachment (i.e. all cells attaching). Results are shown in Tables 1 and 2. The adhesion of cells to the surface having the nanopillars is markedly lower than on the corresponding planar surface.

4) Polystyrene Dot Fabrication Using Embossing 1) 15 nm Dot Fabrication Process

1) Clean 5 mm by 5 mm Silicon substrate, using Opticlear (trademark) citrus fruit oil, acetone, methanol and purified water.
2) Spin a solution of 2.5% Elvacite resist (trademark for polymethylmethacrylate) in xylene at 5000 rpm for 1 minute onto the substrate.
3) Write pattern on resist using electron beam machine (modified Jeol 100CXII).
4) Develop sample in 3:1 isopropanol (IPA): MiBK methylisobutylketone).
5) Reactive ion etch silicon in $SiCl_4$/HBr
6) Remove resist in acetone
7) Emboss into polystyrene at 97° C.

Figure 2:
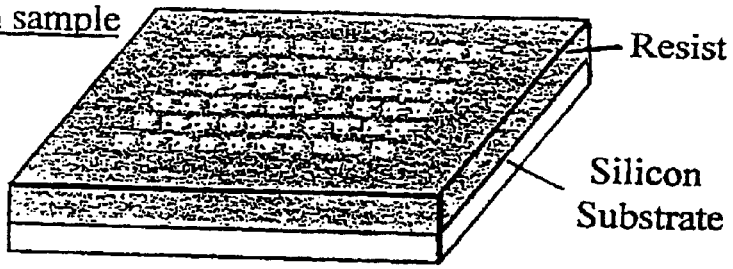
FIG. 2 illustrates the embossing process used to produce an array of pits according to the present invention.
Figure 2:
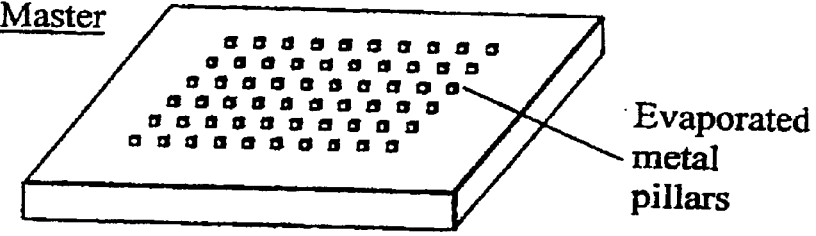
Figure 2:
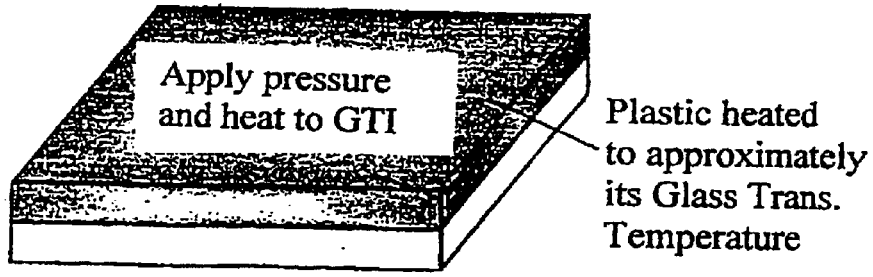
Figure 2:
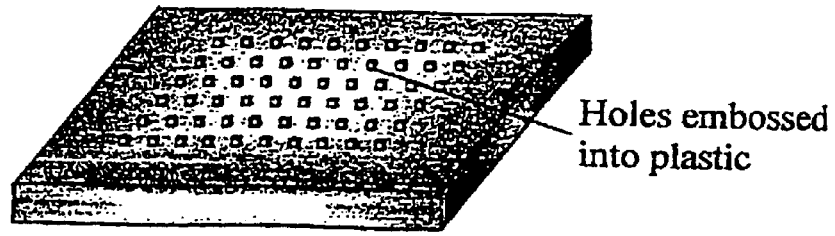

An embossing process to produce an array of pits is shown in FIG. 2.

An embossing process to produce an array of pits is shown in FIG. 2.

2) 50–150 nm Dot Fabrication Process

1) Clean 1 mm, thick perspex (PMMA) substrate in isopropanol.
2) Evaporate 3 nm layer of Nichrome on to the perspex.
3) First write over a 150 $\mu$m by 150 $\mu$m square using the Leica beamwriter mentioned above. The resolution is set to the required period i.e. 300 nm and an electron beam spot size of between 15 nm and 56 nm is used. The dose is 65 $\mu$C/cm$^-$ (this low dose allows fast writing times). The pattern is then repeated out to the desired area of 5 mm by 5 mm.
4) After writing, the Nichrome layer is removed.
5) The sample is developed in 3:1 IPA:MiBK for 10s then rinsed in IPA for a further 10s.
6) The perspex sample is now sputtered with 5 nm layer of Gold Palladium alloy to provide a protective coating.
7) Embossing into polystyrene now takes place at 97° C. for 9 minutes.

TABLE 1

Attachment of cells to pillar topographies. 50 nm high 50 nm center-to-center repeat Epitenon cells.
Cells attached in 1 hour to counting area

|  | Controls (planar surface) | Pillars |
|---|---|---|
| Means | 32.1 (66%) | 10.9 (23%) |
| Standard deviations | 4.4 | 4.7 |

Counting area 864900 $\mu$m$^2$. If adhesion had been 100%, 48 cells would have attached per counting area. Significance test t=11.1 P<0.001 n=22

TABLE 2

Attachment of cells to pillar topographies. 50 nm high 300 nm center-to-center repeat
Rat Epitenon cells
Cells attached in 1 hour to counting area

|  | Controls (planar surface) | Pillars |
|---|---|---|
| Means | 13.2 (28%) | 1.9 (4%) |
| Standard deviations | 5.6 | 2.4 |

Counting area 864900 $\mu$m$^2$. If adhesion had been 100%, 48 cells would have attached per counting area. Significance test t=5.4 P<0.001 n=17

What is claimed is:

1. A biocompatible substrate having a surface comprising an array of projections or pits, said projections or pits being of a size and spacing such that cells have a low tendency to attach to the surface wherein the cross-sectional dimension and/or height of each projection or pit is in the range of about 10–250 nm and the center-to-center spacing of the projections or pits is in the range of about 20–500 nm.

2. The substrate according to claim 1, wherein the cross-sectional dimension and/or height of each projection or pit is in the range of about 20–100 nm.

3. The substrate according to claim 1, wherein the cross-sectional dimension and/or height of each projection or pit is in the range 25–75 nm.

4. The substrate according to claim 1, wherein the projections or pits are circular, oval, square, rectangular or polygonal in cross-section.

5. The substrate according to claim 1, wherein the projections or pits are present in a non-random array.

6. The substrate according to claim 5, wherein the array is a square pattern, a rectangular pattern, a circular pattern or a rosette pattern.

7. The substrate according to claim 1, wherein the center-to-center spacing of the projections or pits is in the range of about 40–300 nm.

8. The substrate according to claim 1, wherein the centre-to-centre spacing of the projections or pits is in the range of about 75–200 nm.

9. The substrate according to claim 1 formed of a biologically resorbable material.

10. The substrate according to claim 1 which additionally comprises an area having a surface topography capable of promoting cell adhesion thereto.

11. The substrate according to claim 10 which further comprises a laminin coating.

12. An implant, graft or prosthesis comprising a substrate according to claim 1.

13. The biocompatible substrate according to claim 1 further comprising an inner surface intended to be wrapped in contact with a ligament and having a surface topography capable of promoting repair of the ligament, and an outer surface having said pattern of projections or pits.

14. A master for mechanical transfer of projections or pits according to claim 1 onto a substrate.

* * * * *